Figure 6:
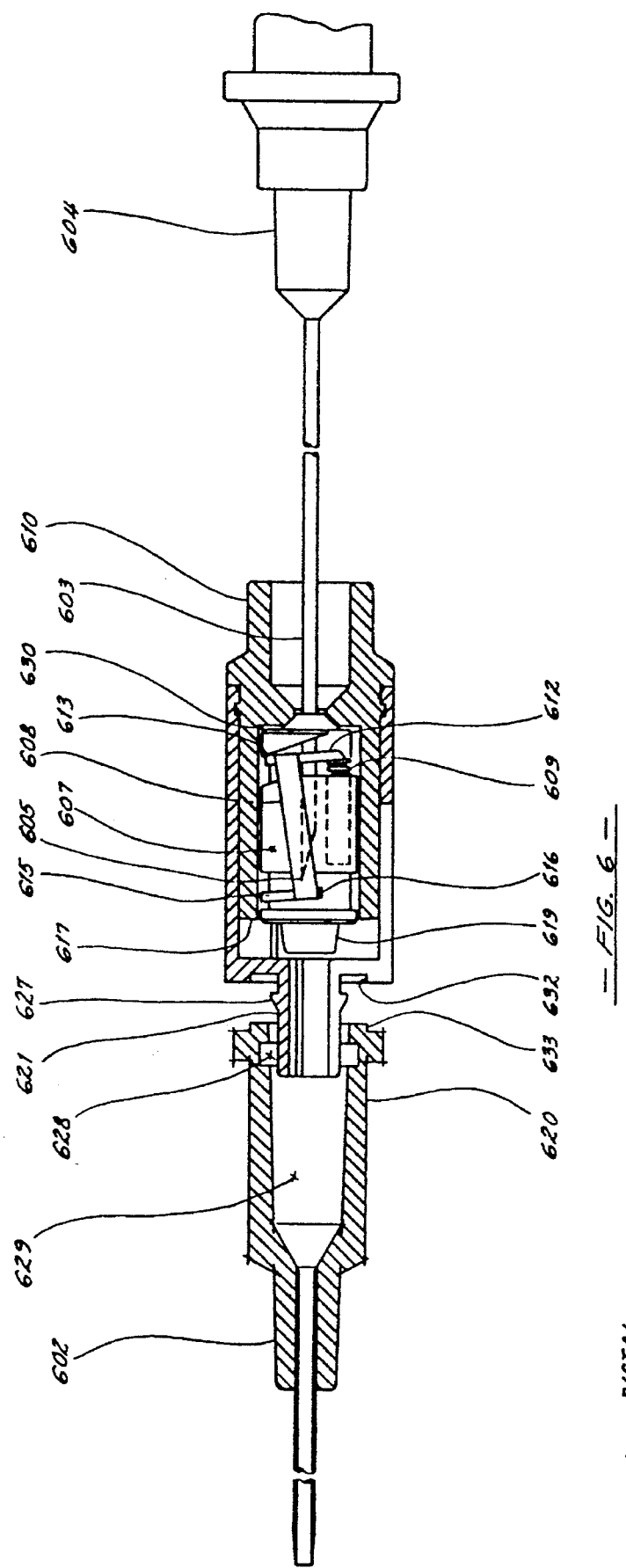

United States Patent [19]

Sircom

[11] Patent Number: 5,458,658
[45] Date of Patent: Oct. 17, 1995

[54] POSITIVE LOCKING NEEDLE-MOUNTED NEEDLE GUARD FOR NEEDLE SUPPORTED CATHETERS

[75] Inventor: Richard C. Sircom, Dartmouth, Canada

[73] Assignee: Sero-Guard Corporation, Ottawa, Canada

[21] Appl. No.: 170,317

[22] Filed: May 6, 1994

Related U.S. Application Data

[63] Continuation-in-part of PCT/CA92/00257, Jun. 17, 1992, which is a continuation-in-part of Ser. No. 730,920, Feb. 1, 1990, Pat. No. 5,322,517, which is a continuation-in-part of Ser. No. 309,305, Feb. 1, 1989, abandoned.

[30] Foreign Application Priority Data

Jun. 17, 1991 [CA] Canada ..................................... 2044818

[51] Int. Cl.⁶ ..................................................... A61M 5/00
[52] U.S. Cl. ........................................... 604/192; 604/263
[58] Field of Search ..................................... 604/263, 192, 604/198, 162, 110, 167, 164

[56] References Cited

FOREIGN PATENT DOCUMENTS

| 352928 | 1/1990 | European Pat. Off. | ............... 604/263 |
| 9008564 | 8/1990 | WIPO | ..................................... 604/263 |
| 9101151 | 2/1991 | WIPO | ..................................... 604/263 |

*Primary Examiner*—John D. Yasko

[57] ABSTRACT

An automatic needle guard for intravenous catheter assemblies, which stores on the insertion needle between the needle base and catheter hub, which attaches by positive engagement to the catheter hub, remains attached while the needle is withdrawn through the needle guard following insertion of the catheter, locks immovably to the needle shaft when the needle tip enters the body of the needle guard, then releases from the catheter hub, allowing the needle guard to be withdrawn along with the needle for safe disposal.

6 Claims, 4 Drawing Sheets

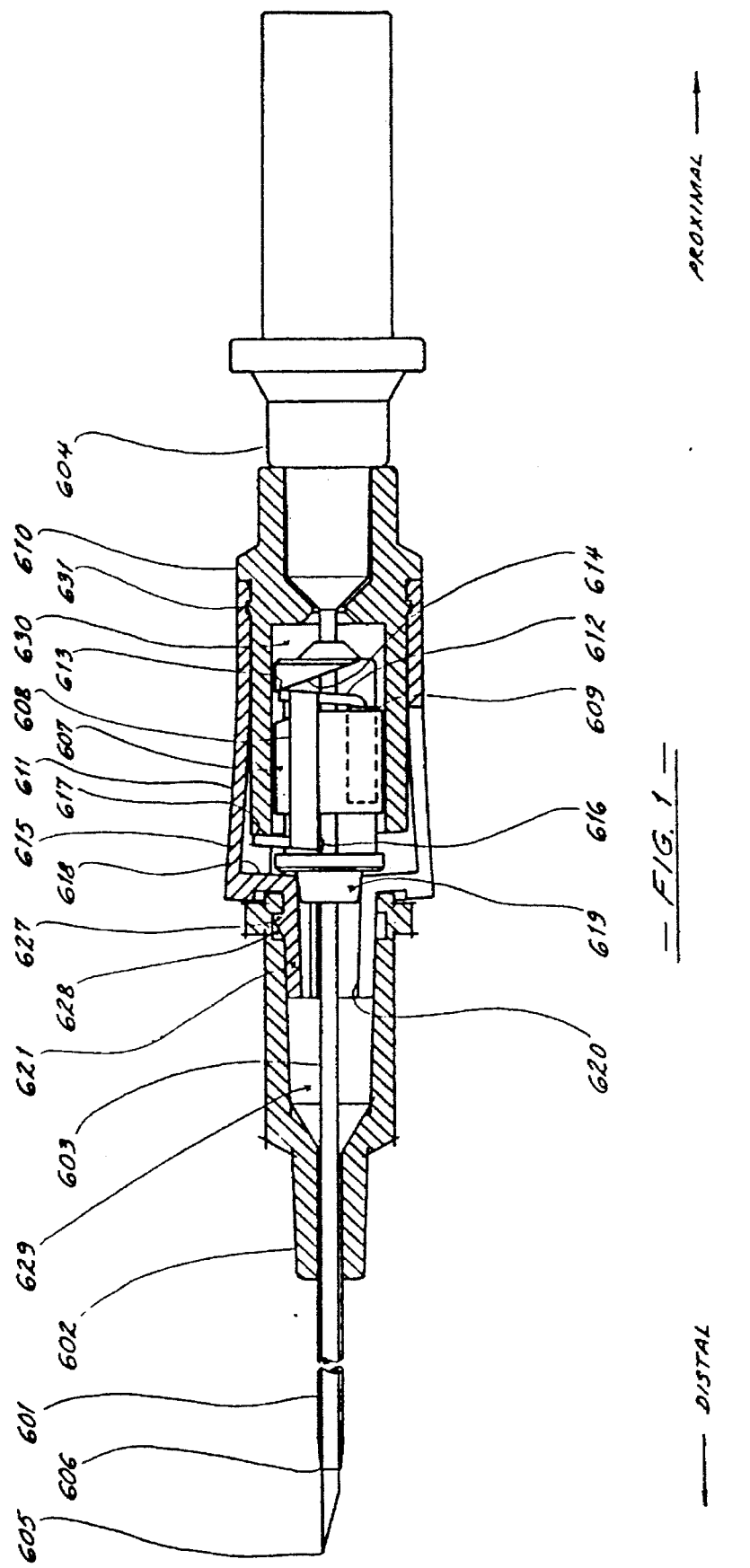

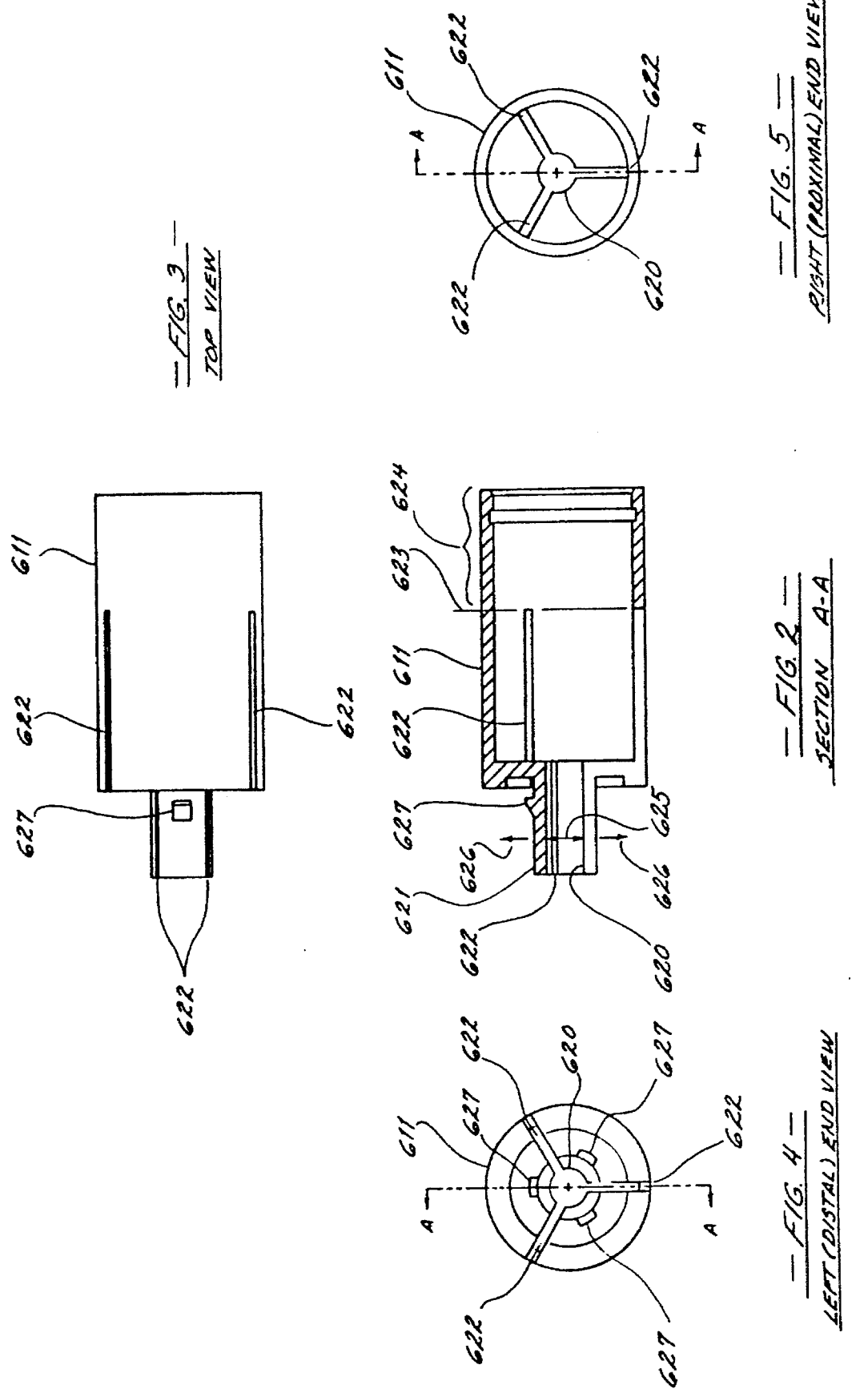

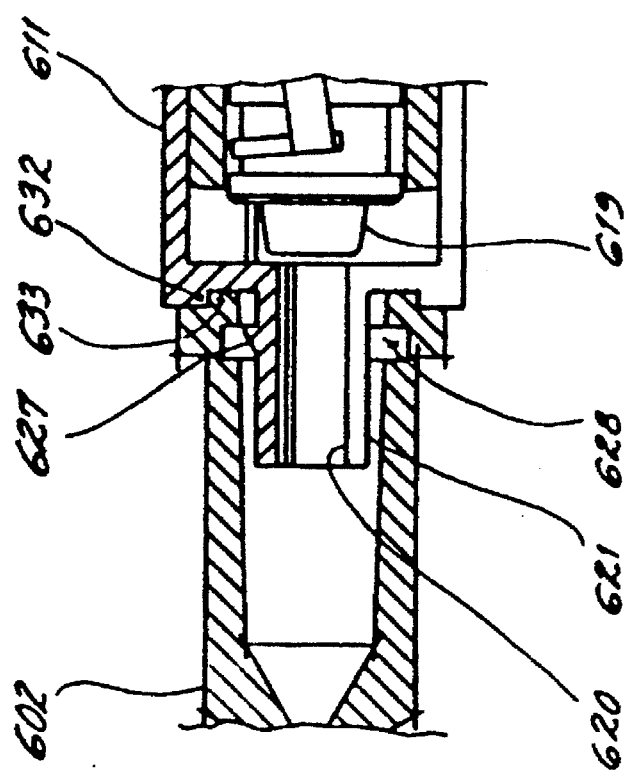
FIG. 7 — (PARTIAL VIEW)

POSITIVE LOCKING NEEDLE-MOUNTED NEEDLE GUARD FOR NEEDLE SUPPORTED CATHETERS

This application is a Continuation-in-Part of PCT application PCT/CA90/00031 filed internationally on Feb. 1, 1989 which is U.S. application Ser. No. 730,920 filed Feb. 1, 1990, issued as U.S. Pat. No. 5,322,517 which is in turn a Continuation-in-Part of U.S. application Ser. No. 309,305 filed 1 Feb. 1989, abandoned.

1. FIELD OF THE INVENTION 1.1 This invention relates to the safe disposal of hypodermic needles by a guard device which protects the needle tip from exposure after use. More particularly, it relates to a mechanism for a tip protector which is storable on the needle and which automatically locks over the end of the needle when slid into position at the needle tip by the user. It relates specifically to a needle guard mounted on and positively engaged with an intravenous catheter and which disengages from the catheter automatically when the needle guard locks over the end of the catheter insertion needle.

1.2 While reference is made herein to "intravenous catheters" these devices are merely exemplary. This invention relates to all forms of needle-supported cannulas, such as those used as catheters.

2. BACKGROUND TO THE INVENTION 2.1 The type of needle guard to which this invention relates has been described in Patent Cooperation Treaty application No. PCT/CA90/00031 published on Aug. 9, 1990 under international publication number WO 90/08564.

2.2 This cited prior application describes a range of configurations for needle guard devices which are stored at the base of a needle and which automatically engage with and cover the tip of a needle when moved to the tip.

2.3 Two references which do provide self-deploying needle guards on an intravenous catheter are:
   (1) European patent application No. 89306957.5 of Lemieux published 31 Jan., 1990 as No. 0 352 928; and
   (2) PCT application PCT/US 90/03987 of McLees published on 7 Feb., 1991 as WO 91/01151.
Neither of these applications permit utilization of a standard, featureless cylindrical needle.

2.4 One embodiment in the cited prior PCT patent application PCT/CA 90/00031 relates to the installation of the needle guard on an intravenous catheter assembly, in which the needle guard is frictionally retained on the base or hub of the catheter, until the needle guard locks over the tip of the insertion needle, as the latter is withdrawn from the catheter. Continued needle withdrawal motion is then transmitted to the locked needle guard, and additional withdrawal force overcomes the frictional grip of the needle guard on the catheter hub, allowing the needle guard to separate from the hub for disposal with the needle.

2.5 This embodiment requires that the user of the intravenous assembly hold the catheter hub with hand A while withdrawing the needle by pulling on its base with hand B. It thus requires no change in the user's accustomed manipulative procedure used with an ordinary catheter assembly.

2.6 However, if the user withdraws the needle by using hand B grip and pull the needle guard instead of the needle base, the needle guard will separate prematurely from the catheter while the needle point is still outside the body of the needle guard, and therefore unprotected. This malfunction defeats the purpose of the needle guard.

2.7. The above embodiment further requires that the withdrawal force required to overcome the frictional grip on the catheter hub of the locked needle guard be significantly greater than the frictional drag between the needle and the needle guard when the latter is being slid along the needle shaft during the withdrawal motion. This is to ensure that the needle guard does not separate from the catheter hub before the needle guard locks over the needle tip. However, this frictional separation force must not be excessive, as it may cause the catheter to be jerked involuntarily toward and into the patient by the user's hand A at the moment of separation, causing possible injury. These conflicting frictional requirements place significant constraints on the design of the needle guard assembly.

2.8 The invention described herein relates to a further embodiment of the above prior applications whereby the needle guard is retained on the catheter hub by a positive engagement means between the needle guard and the hub, instead of by friction. This engagement means is released only after the needle guard has locked over the needle tip, allowing the needle guard to separate from the catheter hub without significant further withdrawal effort.

2.9 With this embodiment, if the user's hand B accidentally grips the needle guard instead of the needle base during withdrawal, the user will be unable to separate the needle guard from the catheter hub, and must transfer the grip of hand B correctly to the needle base before he can withdraw the needle.

2.10 Furthermore, if hand A should accidentally grip the needle guard instead of the catheter in order to restrain the catheter during withdrawal of the needle, the needle will draw out and the needle guard will lock in the normal way. This will release the needle guard to separate from the catheter hub with little or no further pulling effort. It is therefore immaterial whether the catheter is restrained with hand A by holding its hub, or by holding the needle guard.

2.11 With this embodiment, the needle guard must lock to the needle shaft, covering the needle tip, before the needle guard can be released from its positive engagement with the catheter hub. Thus the needle tip cannot be exposed under any circumstances, following attachment of the needle guard and needle to the catheter hub.

2.12 Two references which do provide self-deploying needle guards on an intravenous catheter are:
   (1) European patent application No. 89306957.5 of Lemieux published 31 Jan., 1990 as No. 0 352 928; and
   (2) PCT application PCT/US 90/03987 of McLees published on 7 Feb., 1991 as WO 92/01151.
Neither of these applications permit utilization of a standard, featureless cylindrical needle.

3. SUMMARY OF THE INVENTION 3.1 According to this invention, a needle guard is provided that may be installed at the base of a constant diameter insertion needle of an intravenous catheter assembly and which remains positively attached at the base of the catheter until the guard is deployed at the needle tip.

3.2 The preferred embodiment needle guard mechanism is of the canted locking plate type described in the cited PCT application PCT/CA 90/00031, comprising:
   3.2.1 A body having an axial needle passageway extending the length of the body, and also having other laterally-accessible component cavities.

3.2.2 A canting lever with a locking plate at its one end and a sensing plate at its other, installed in one of the above component cavities.

3.2.3 A spring, mounted in one of the above component cavities, and arranged to hold the sensing end of the lever in contact with the side of the insertion needle shaft.

3.2.4 A shell of one or more pieces, enclosing the body and its contained lever and spring.

3.2.5 The shell of the present invention will be described herein as comprising an inner shell and a partially surrounding outer shell, with the outer shell being generally the more distal of the two.

3.3 In a widely used form, the catheter assembly includes a flexible catheter cannula or sheath, attached to a base containing a tapered internal bore, which is used for the attachment of other devices after the catheter has been inserted into the patient. For use with this invention, this internal bore has an annular groove formed in its wall near the larger, proximal, or entry end of the bore.

3.4 The outer shell of this invention includes an axial extension from its distal end of generally cylindrical form, which extends into the tapered bore of the catheter hub, reaching past the annular groove formed therein. This axial extension, referred to hereinafter as the retaining plug, has a central axial internal bore to accommodate the insertion needle, and is divided into a plurality of cylindrical sectors by longitudinal radial slots formed therein, with the slots extending into the larger proximal portion of the outer shell. These slots divide the cross-section of the outer shell so as to impart radial flexibility to the cylindrical sectors of the retaining plug, which can flex in cantilever from their attachment to the unslotted proximal portion of the outer shell.

3.5 Each sector of the retaining plug carries on its outer cylindrical surface a barb. The longitudinal section of each barb may typically resemble a so-called buttress thread or more familiarly, one half of an arrowhead, with the arrow pointing distally along the needle axis.

3.6 The dimensions of the retaining plug and the barbs are such as to allow free axial passage of the barbs within the proximal portion of the internal bore of the catheter hub, when the retaining plug alone is inserted therein.

3.7 Each barb on the retaining plug is located so as to fit into the annular groove in the catheter hub when the retaining plug is expanded radially by the axial insertion of a suitable cylindrical expansion member into the central cylindrical bore of the retaining plug. With the retaining plug thus expanded, it is retained axially within the catheter hub by the engagement of the barbs with the annular groove in the hub.

3.8 The above expansion member, referred to hereinafter as a spigot, consists of a substantially cylindrical axial extension of the distal end of the body of the needle guard mechanism.

3.9 Prior to use of the catheter assembly, the needle guard is held in the unlocked state by the presence of the needle shaft within the needle guard body, with the needle holding the sensing plate of the lever against the urging of the spring in a position radially removed from the needle axis. This is described more fully in the cited prior applications. A radial extension of the sensing plate engages the distal end face of the inner shell, holding the lever and the body axially at the distal end of the cylindrical internal cavity of the shell.

3.10 In this position of the body, the spigot of the latter is held in position inside the internal bore of the retaining plug, so as to expand it into locking engagement with the catheter hub as described in 3.7 above.

3.11 On withdrawal of the needle following insertion of the catheter, the passage of the needle tip past the sensing plate of the lever allows the sensing plate to move radially inward under urging of the spring, initiating the locking action of the needle guard, as described in the cited prior applications.

3.12 This inward motion of the sensing plate disengages the letter from the end face of the inner shell, allowing axial motion of the lever and body in a proximal direction within the internal cavity of the shell. This motion withdraws the spigot from the internal bore of the retaining plug, allowing it to collapse inwardly, disengaging the barbs from the groove in the internal bore of the catheter hub. This allows separation of the needle guard from the catheter, completing the operational sequence for the device.

4. SUMMARY OF THE FIGURES 4.1 FIG. 1 is a longitudinal sectional view of a needle guard employing a canted-plate locking lever, a described in the cited prior applications, and installed on an intravenous catheter assembly. The assembly is shown in its pre-use or unlocked state.

4.2 FIG. 2 is a detail view of the outer shell of the needle guard, shown in longitudinal section.

4.3 FIG. 3 is an exterior top view of FIG. 2.

4.4 FIG. 4 is an exterior distal end view of FIG. 2.

4.5 FIG. 5 is an exterior proximal end view of FIG. 2.

4.6 FIG. 6 is a longitudinal sectional view of the needle guard of FIG. 1, shown in its after-use or locked state, with the needle guard locked over the needle tip and almost completely withdrawn from the catheter hub.

4.7 FIG. 7 is a partial longitudinal sectional view of the junction between the needle guard and the catheter hub immediately following locking of the guard but before removal of the guard from the catheter hub.

5. DESCRIPTION OF THE PREFERRED EMBODIMENTS 5.1 In FIG. 1 is shown a typical intravenous catheter assembly, comprising flexible cannula 601 mounted in catheter hub 602, and insertion needle 603 mounted in needle base 604. The needle is shown fully inserted in the assembly in its pre-use state, with the needle tip 605 extending slightly beyond the cannula tip 606 in the usual way.

5.2 The needle guard assembly comprises body 607, lever 608, spring 609, inner shell 610, and outer shell 611. The latter two shell portions are typically held together by snap connection 631.

5.3 The operation of the needle guard in sensing the entry of the needle tip 605 into the guard body and the subsequent locking action are described in the cited prior applications.

5.4 In the unlocked state a shown, spring 609 presses against the lower end of locking plate 612 of lever 608, which serves as a needle engagement means 612, causing it to tend to pivot counter-clockwise about its upper point of contact 613 with the sloped internal face 614 of body 607. This rotation is prevented by sensing plate 615 at the opposite end of lever 608 coming into contact with needle 603 at point 616.

5.5 With sensing plate 615 positioned as shown, lever 608 is restrained from moving to the right relative to the shell by the upper end of plate 615 coming in contact with the face 617 of inner shell 610.

5.6 The reaction of spring 609 acting against the immovable lever 608 presses body 607 to the left against internal face 618 of outer shell 611, thus holding spigot 619 in bore 620 of retaining plug 621.

5.7 Referring to FIGS. 2, 3, 4 and 5, which depict outer shell 611 in isolation, retaining plug 621 extends from the closed left end of the outer shell, and is divided into three or more sections by slots 622, which extend into the larger portion of the outer shell to point 623. The shell is-molded of a suitable compliant plastic material.

5.8 These longitudinal sections of shell function a cantilever beams, able to flex radially from their point of common attachment to end 624 of the outer shell 611. By applying internal expansion 625 to the internal bore 620 of retaining plug 621, the latter may be expanded in the directions 626.

5.9 Referring to FIG. 1, spigot 619, or spigot means 621, holds retaining plug 621 in an expanded state, so that barbs 627, which serve as catheter hub engagement means 627, engage annular groove 628 in the wall of catheter hub 602. This holds retaining plug 621 axially in the tapered bore 629 of catheter hub 602.

5.10 During withdrawal of the needle following insertion of the cannula, the retaining plug 621 is maintained in the expanded state by spigot 619, until the needle tip 605 reaches the proximal side of sensing plate 615, as shown in FIG. 6. This removes the radial restraint from point 616 at the lower end of the sensing plate 615, allowing spring 609 to rotate lever 608 in a counter-clockwise direction about its pivot point 613, to assume the locked position shown. The accompanying locking action is fully described in the cited prior applications.

5.11 With sensing plate 615 in its locked position as shown in FIG. 6, its upper end no longer engages end face 617 of inner shell 610. This frees lever 608 to follow the continued withdrawal motion of needle 603 to the right, and this motion is imparted through pivot point 613 to body 607, moving it to the right in the cavity 630 of inner shell 610.

5.12 The rightward motion of body 607 withdraws spigot 619 from internal bore 620 of retaining plug 621, allowing the latter to collapse inwardly because of its intrinsic compliance, and disengaging barbs 627 from groove 628 in catheter hub 602. This allows the entire needle guard assembly to be withdrawn from the catheter hub as shown, to be disposed of along with the needle.

5.12 Spigot 619 may be formed with a slight taper, with the diameter diminishing in the distal direction. This will allow the inwardly-collapsing effort of the several compliant sections of retaining plug 621 to assist the effort of withdrawing the spigot from retaining plug 621. The paper may be made sufficiently steep that the spigot can be ejected entirely by this inwardly-collapsing action, without requiring any further withdrawal effort by the user.

5.14 To ensure that the needle guard releases freely from the catheter hub after the needle guard locks, retaining plug 621 must be held centered in the internal bore 629 of the catheter hub 602, so that barbs 627 do not catch on the edge of groove 628 during withdrawal. As shown in partial view FIG. 7, this alignment is obtained by the engagement of a short cylindrical overhang 632 on the distal end of outer shell 611 with a mating cylindrical shoulder 633 on the proximal end of catheter hub 602, when spigot 619 has withdrawn from the internal bore 620 of retention plug 621, and the outer shell has collapsed inwardly. This radial alignment is maintained until the barbs 627 have been axially withdrawn out of alignment with groove 628, and therefore can no longer accidentally engage the groove, as shown in FIG. 6.

6. CONCLUSION 6.1 The foregoing has constituted a description of a specific embodiment showing how the invention may be applied and put into use. This embodiment is only exemplary. The invention in its broadest, and more specific aspects, is further described and defined in the claim which now follows.

The embodiments of the invention for which an exclusive right is claimed are follows:

1. A catheter assembly comprising a catheter cannula 601 with catheter hub 602 and an insertion needle 603 of constant diameter having a tip 605, such assembly being provided with a needle guard comprising:

(a) a body 607 mounted on the needle 603;

(b) needle engagement means 612 for automatically engaging the body 607 with the needle 603 against further removal from the needle 603 when the needle guard is slid to cover the needle tip 605;

(c) catheter hub engagement means 627 actionably coupled to said body 607 for positively engaging said body 607 to the hub 602 of the catheter 601 so long as the needle guard is positioned rearwardly of the needle tip 605 characterized in that said catheter hub engagement means 627 is displaceably distinct from said body 607 and is held in engagement with the hub 602 of the catheter 601 by the body 607 so long as the needle engagement means 612 remains non-engaged with the needle and automatically disengages from the catheter hub 602 once the needle engagement means 612 has engaged with the needle 603.

2. A catheter assembly as in claim 1 characterized in that said body 607 is displaceable rearwardly from the needle tip 605, in the axial direction of the needle 603, to effect release of the catheter hub engagement means 627 and disengagement of the needle guard from the catheter hub 602.

3. A catheter assembly as in claim 1 characterized in that said catheter hub engagement means 627 is held in engagement with the hub 602 by a spigot means 619 carried on said body portion 607.

4. A catheter assembly as in claim 3 characterized in that said catheter hub 602 is provided with an interior groove 628 which is engaged by said catheter hub engagement means 627 to hold the body 607 in engagement with the catheter hub 602.

5. A catheter assembly as in claim 4 characterized in that said catheter hub engagement means 627 comprises a barb 627 carried on a retaining plug 621 that is held in an expanded state by the spigot means 621 prior to the disengagement of the body 607 from the catheter hub 602.

6. A catheter assembly comprising a catheter cannula 601 with catheter hub 602 and an insertion needle 603 having an outside surface of constant diameter and a tip 605 at its forward end, such assembly being provided with a needle guard positioned on said needle 603 comprising:

(a) needle engagement means 612 for automatically engaging the needle guard with the outside surface of the needle 603 against further removal of the needle guard from the needle 603 when the needle guard is slid to cover the needle tip 605;

(b) catheter hub engagement means 627 carried by said needle guard and maintained by a sensing plate means 615 in positive engagement with the hub 602 of the catheter 601 so long as the sensing plate means 615 is positioned rearwardly of the needle tip 604; and (c) spring means carried within said needle guard and positioned to urge said sensing plate means 615 to become displaced when the needle tip 604 is moved past the sensing plate means 615 and the needle guard becomes engaged with the needle 603, whereupon said catheter hub engagement means 627 will disengage from the hub 602 of the catheter 601.

* * * * *